US008923975B2

(12) United States Patent
Bradley (10) Patent No.: US 8,923,975 B2
(45) Date of Patent: Dec. 30, 2014

(54) METHOD FOR DIRECT MODULATION OF THE DORSOLATERAL FUNICULUS

(71) Applicant: Boston Scientific Neuromodulation Corporation, Valencia, CA (US)

(72) Inventor: Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 251 days.

(21) Appl. No.: 13/708,742

(22) Filed: Dec. 7, 2012

(65) Prior Publication Data
US 2013/0150920 A1 Jun. 13, 2013

Related U.S. Application Data

(60) Provisional application No. 61/569,216, filed on Dec. 9, 2011.

(51) Int. Cl.
*A61N 1/00* (2006.01)
*A61N 1/36* (2006.01)
*A61N 1/05* (2006.01)

(52) U.S. Cl.
CPC ........ *A61N 1/36071* (2013.01); *A61N 1/36146* (2013.01); *A61N 1/0553* (2013.01); *A61N 1/36164* (2013.01); *A61N 1/36171* (2013.01); *A61N 1/36185* (2013.01)
USPC ............................................. 607/46; 607/117

(58) Field of Classification Search
CPC ............ A61N 1/36071; A61N 1/0551–1/0558
USPC .................................................... 607/46, 117
See application file for complete search history.

(56) References Cited

U.S. PATENT DOCUMENTS

| | | | |
|---|---|---|---|
| 5,501,703 A * | 3/1996 | Holsheimer et al. | 607/46 |
| 7,650,184 B2 | 1/2010 | Walter | |
| 7,742,810 B2 | 6/2010 | Moffitt et al. | |
| 8,019,439 B2 | 9/2011 | Kuzma et al. | |
| 2007/0021802 A1* | 1/2007 | Heruth et al. | 607/46 |
| 2007/0142863 A1 | 6/2007 | Bradley | |
| 2007/0168004 A1 | 7/2007 | Walter | |
| 2007/0168007 A1 | 7/2007 | Kuzma et al. | |
| 2008/0294226 A1 | 11/2008 | Moffitt et al. | |
| 2009/0270935 A1* | 10/2009 | Zhao et al. | 607/14 |
| 2011/0009923 A1 | 1/2011 | Lee | |

\* cited by examiner

*Primary Examiner* — Michael Kahelin
*Assistant Examiner* — Mallika D Fairchild
(74) *Attorney, Agent, or Firm* — Lowe Graham Jones PLLC; Bruce E. Black (57) ABSTRACT

A method for treating a patient suffering from chronic neuropathic pain, comprises epidurally applying electrical stimulation energy to a dorsolateral funiculus of the patient, thereby treating the chronic neuropathic pain. The method may further comprise increasing the activation threshold of a side-effect exhibiting neural structure relative to the activation threshold of the dorsolateral funiculus of the patient, wherein the electrical stimulation energy is applied to the dorsolateral funiculus of the patient while the activation threshold of the neural structure relative to the dorsolateral funiculus is increased, thereby treating the chronic neuropathic pain without stimulating the neural structure.

20 Claims, 7 Drawing Sheets

METHOD FOR DIRECT MODULATION OF THE DORSOLATERAL FUNICULUS

RELATED APPLICATION DATA

The present application claims the benefit under 35 U.S.C. §119 to U.S. provisional patent application Ser. No. 61/569,216, filed Dec. 9, 2011. The foregoing application is hereby incorporated by reference into the present application in its entirety.

FIELD OF THE INVENTION

The present invention relates to tissue stimulation systems, and more particularly, to spinal cord stimulation systems.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic neuropathic pain syndromes, and the application of spinal cord stimulation has expanded to include additional applications, such as angina pectoralis, peripheral vascular disease, and incontinence, among others. Spinal cord stimulation is also a promising option for patients suffering from motor disorders, such as Parkinson's Disease, Dystonia and essential tremor.

An implantable SCS system typically includes one or more electrode-carrying stimulation leads, which are implanted at a stimulation site in proximity to the spinal cord tissue of the patient, and a neurostimulator implanted remotely from the stimulation site, but coupled either directly to the stimulation lead(s) or indirectly to the stimulation lead(s) via a lead extension. The neurostimulation system may further include a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer (CP), which typically includes a general purpose computer, such as a laptop, with a programming software package installed thereon.

Thus, programmed electrical pulses can be delivered from the neurostimulator to the stimulation lead(s) to stimulate or activate a volume of the spinal cord tissue. In particular, electrical stimulation energy conveyed to the electrodes creates an electrical field, which, when strong enough, depolarizes (or "stimulates") the neural fibers within the spinal cord beyond a threshold level, thereby inducing the firing of action potentials (APs) that propagate along the neural fibers to provide the desired efficacious therapy to the patient.

As discussed, SCS may be utilized to treat patients suffering from chronic neuropathic pain. To this end, electrical stimulation is generally applied to the dorsal column (DC) nerve fibers, which is believed to inhibit the perception of pain signals via the gate control theory of pain by creating interneuronal activity within the dorsal horn that inhibits pain signals traveling from the dorsal root (DR) neural fibers that innervate the pain region of the patient up through the dorsolateral funiculus of the spinal cord to the brain. Consequently, stimulation leads are typically implanted within the dorsal epidural space to provide stimulation to the DC nerve fibers. Such techniques of treating pain may be beneficial for some patients initially, but it has decreasing efficiency over time. This may be because the natural neural interconnections may be minimally present in some patients, or because the natural neural interconnections may be rendered ineffective by the pathological condition.

SUMMARY OF THE INVENTION

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present invention are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
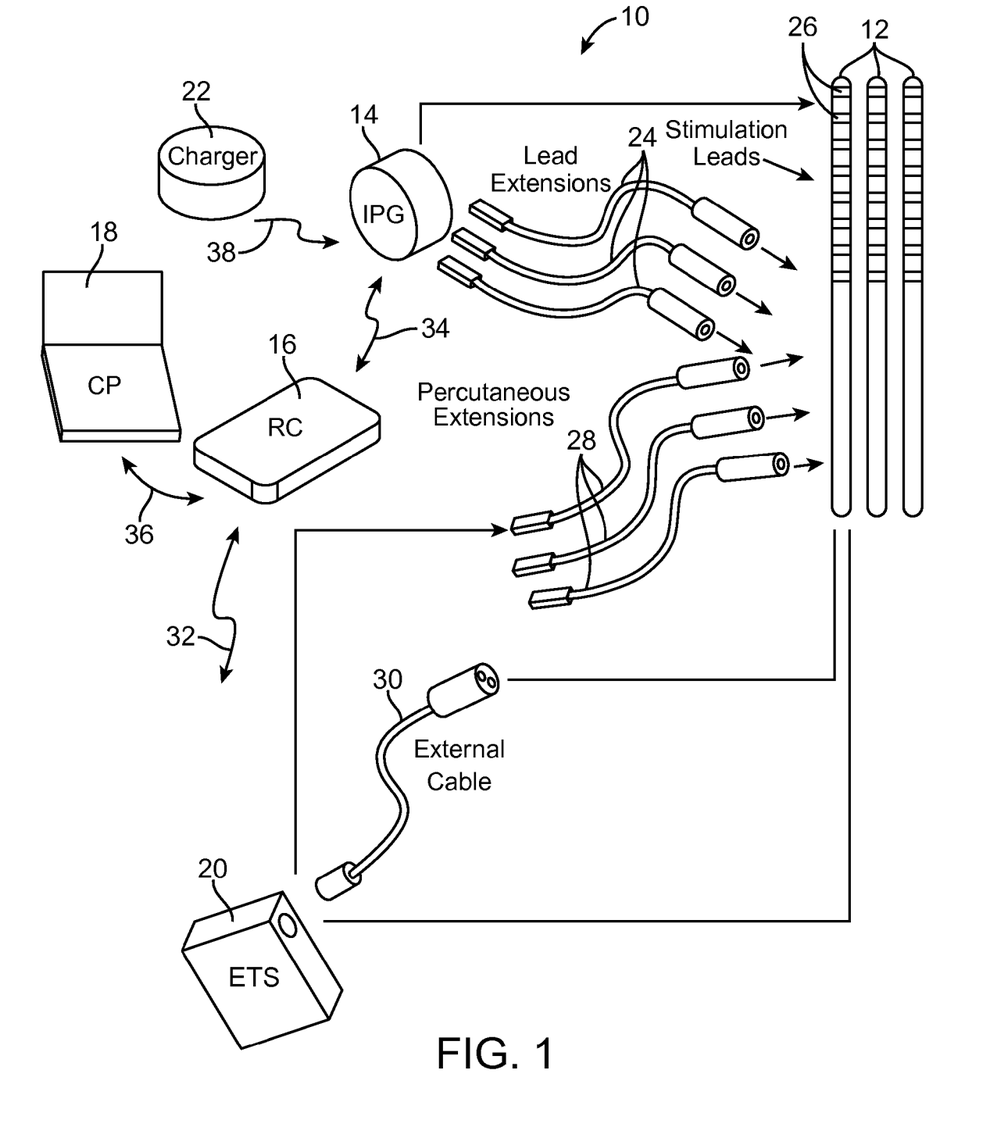
FIG. 1 is a plan view of a Spinal Cord Stimulation (SCS) system constructed in accordance with one embodiment of the present inventions.

Turning first to FIG. 1, an exemplary SCS system 10 generally comprises a plurality of stimulation leads 12 (in this case, three), an implantable pulse generator (IPG) 14 (or alternatively RF receiver-stimulator), an external remote control RC 16, a Clinician's Programmer (CP) 18, an External Trial Stimulator (ETS) 20, and an external charger 22.

The IPG 14 is physically connected via one or more lead extensions 24 to the stimulation leads 12, which carry a plurality of electrodes 26 arranged in an array. The stimulation leads 12 are illustrated as percutaneous leads in FIG. 1, although as will be described in further detail below, a surgical paddle lead can be used in place of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
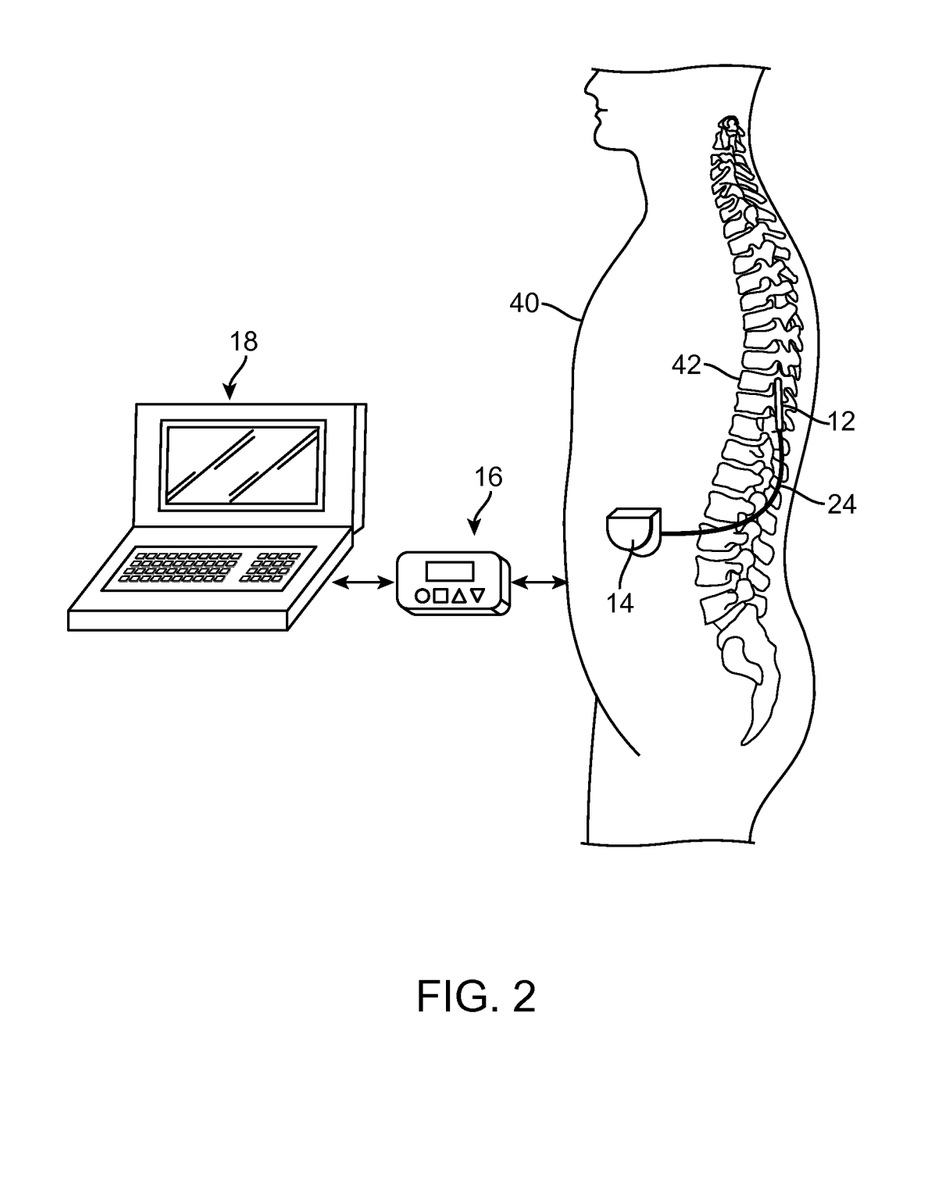
FIG. 2 is a plan view of the SCS system of FIG. 1 in use within a patient.

As shown in FIG. 2, the stimulation leads 12 are implanted within the spinal column 42 of a patient 40. The preferred placement of the electrode leads 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
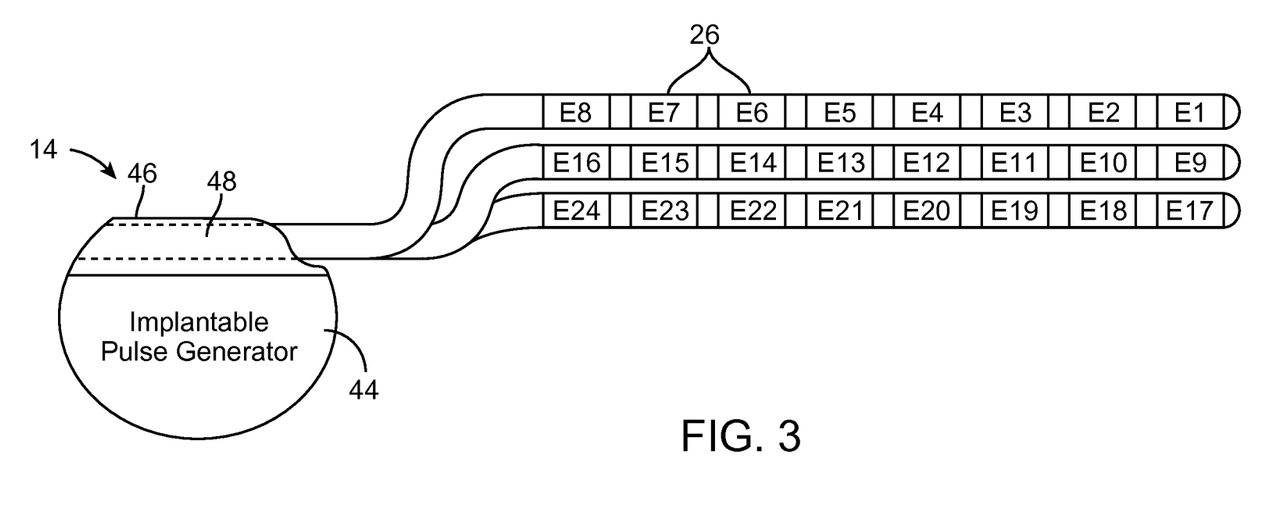
FIG. 3 is a plan view of an implantable pulse generator (IPG) and three percutaneous stimulation leads used in the SCS system of FIG. 1.

Referring now to FIG. 3, the external features of the stimulation leads 12 and the IPG 14 will be briefly described. Each of the stimulation leads 12 has eight electrodes 26 (respectively labeled E1-E8, E9-E16, and E17-E24). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 4:
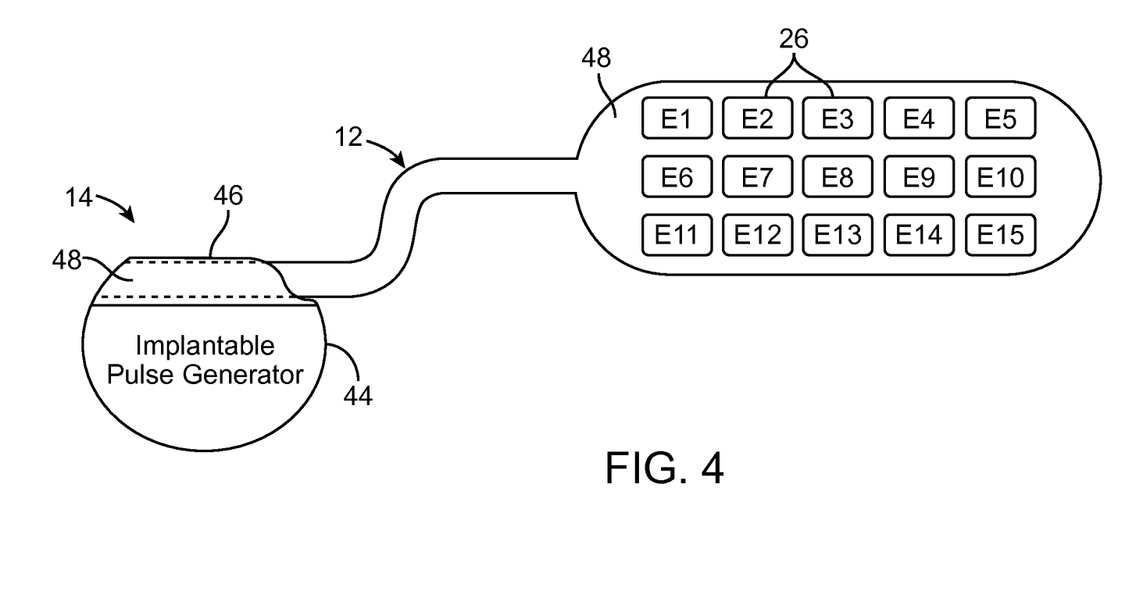
FIG. 4 is a plan view of an implantable pulse generator (IPG) and a surgical paddle lead used in the SCS system of FIG. 1.

Alternatively, as illustrated in FIG. 4, the stimulation lead 12 takes the form of a surgical paddle lead on which electrodes 26 are arranged in a two-dimensional array in three columns (respectively labeled E1-E5, E6-E10, and E11-E15) along the axis of the stimulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

In each of the embodiments illustrated in FIGS. 3 and 4, the IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the stimulation leads 12 mate in a manner that electrically couples the electrodes 26 to the internal electronics (described in further detail below) within the outer case 40. To this end, the connector 42 includes one or more ports (three ports 44 or three percutaneous leads or one port for the surgical paddle lead) for receiving the proximal end(s) of the stimulation lead(s) 12. In the case where the lead extensions 24 are used, the port(s) 44 may instead receive the proximal ends of such lead extensions 24.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and the case 40. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of 15 the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 5:
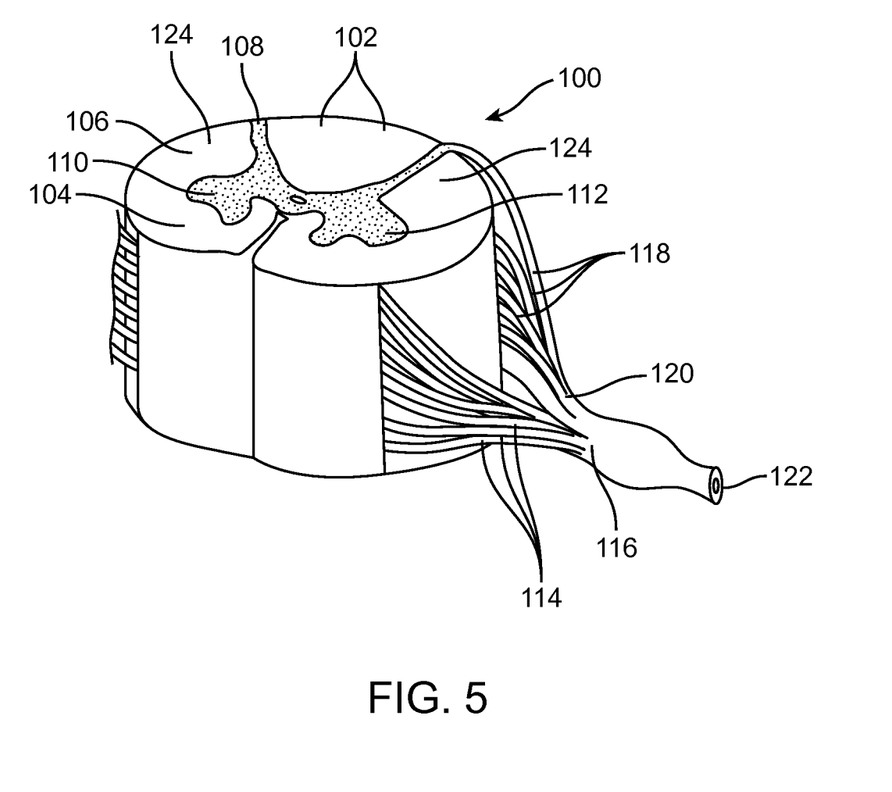
FIG. 5 is a peripheral view of the spinal cord and spinal nerves.
Figure 6:
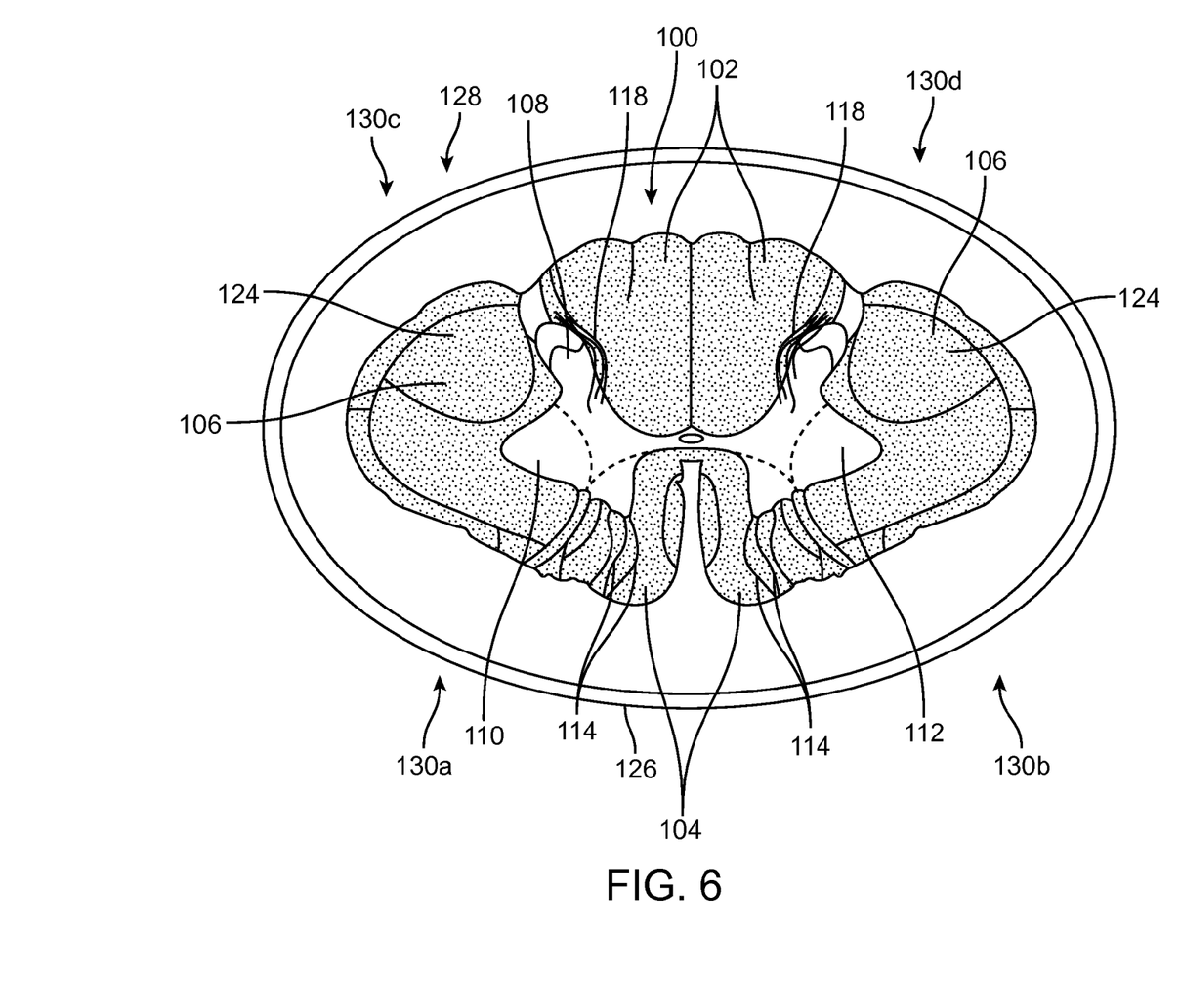
FIG. 6 is a cross-sectional view of the spinal cord.

Referring now to FIGS. 5 and 6, the portions of the spinal cord 100 that are relevant to the present inventions will be described. The spinal cord 100 is divided into three columns: the dorsal column 102, the ventral column 104, and the lateral column 106. Similarly, the butterfly-shaped gray matter of the spinal cord 100 is divided into the dorsal horn 108, the ventral horn 110, and the lateral horn 112.

A group of motor nerve rootlets (ventral root (VR) nerve fibers) 114 branch off of the ventral horn 110 and combine to form the ventral root 116. Similarly, a group of sensory nerve rootlets (dorsal root (DR) nerve fibers) 118 branch off of the dorsal horn 108 and combine to form the dorsal root 120. The dorsal root 120 and the ventral root 116 combine to form the spinal nerve 122, which innervates peripheral regions (e.g., arms, legs, etc.) of the patient's body. A number of spinal nerves branch off the spinal cord. In each patient, there are eight cervical spinal nerves designated C1-C8, twelve thoracic spinal nerves designated T1-T12, five lumbar spinal nerves designated L1-L5, and five sacral spinal nerves designated S1-S5.

The dorsolateral funiculus 124 is a neural pathway lying in the dorsolateral region of the spinal cord, and is included within the lateral column 106. The dorsolateral funiculus 124 contains several functioning ascending and descending tracts, including the dorsospinocerebellar tract, which controls proprioception, the spinocervical tract, which controls coarse mechanoreception, the corticospinal tract, which controls voluntary and fine motor control, and the descending inhibitory tract, which controls pain transmission. It is known that the supraspinal centers, including the periaqueductal grey, periventricular gray, rostroventral medulla/nucleus raphe magnus, and anterior pretectal nucleus, manages the descending inhibition of pain via release of serotonin, norepinephrine, and enkephalin in the dorsal horn. The descending inhibitory tract of the dorsolateral funiculus 124, which include relatively large diameter nerve tracts and thus are easily stimulated, runs along the outer surface of the dorsolateral funiculus 124. Thus, the descending inhibitory tract of the dorsolateral funiculus 124 offers an attractive target for managing pain. The spinal cord 100 is enclosed by a dura mater 126, with an epidural space 128 surrounding the dura mater 126. The epidural space 128 may be topologically divided into four quadrants: a left ventral-lateral quadrant 130a, a right ventral-lateral quadrant 130b, a left dorsal-lateral quadrant 130c, and a right dorsal-lateral quadrant 130d.

In conventional SCS techniques, stimulation is applied to the dorsal column 102 of the spinal cord 100 to treat chronic neuropathic pain, and accordingly, stimulation leads are positioned in the dorsal region of the epidural space 128. As opposed to the conventional systems, the embodiments of the present invention modulate the dorsolateral funiculus 124 of the spinal cord 100 for treating disorders such as chronic neuropathic pain. To this end, the stimulation lead(s) 12 are preferably implanted within the patient lateral to the midline of the spinal cord 100 within the epidural space 128, such that the tip(s) of the stimulation lead(s) 12, and thus some of the electrodes 26, are located in either of the dorsal-lateral quadrants 130c, 130d of the epidural space 128 adjacent the dorsolateral funiculus 124 of the spinal cord 100.

Thus, electrical stimulation energy can be epidurally applied by the stimulation lead(s) to stimulate the dorsolateral funiculus 124, thereby treating chronic neuropathic pain. The distal end(s) of the stimulation lead(s) 12 are preferably located at a position along the spinal cord 100 rostral to the dorsal root 120 that innervates the pain region of the patient. In this manner, electrical stimulation occurs at the region of the dorsolateral funiculus 124 that is rostral to this innervating dorsal root 120, such that inhibitory signals are generates as conveyed to the region of the dorsal horn associated with the particular innervating dorsal root 120. As briefly stated above, the descending pain inhibitory tract is located on the outer surface of the dorsolateral funiculus 124, and therefore, more easily stimulated than the other tracts within the dorsolateral funiculus 124. However, if the magnitude of the stimulation is too high, it is possible that the neural axons of the spinocerebellar tracts may be inadvertently stimulated, thereby causing side effects in the form of involuntary motor movements. If this occurs, the stimulation amplitude may be turned down such that electrical field modulation of the dorsolateral funiculus 124 occurs without necessarily creating a preponderance of action potentials in the neural axons of the dorsolateral funiculus 124.

During application of the stimulation energy to the dorsolateral funiculus 124, the activation threshold of neural structures (e.g., the DR nerve fibers 118 under which the dorsolateral funiculus 124 generally lies) relative to the activation threshold of the dorsolateral funiculus 124 is preferably increased, so that the neural structures are not inadvertently stimulated. As will be described in further detail below, different techniques can be used to increase the activation thresholds of these neural structures relative to the activation threshold of the dorsolateral funiculus 124. In one embodiment, the stimulation leads(s) 12 are located within the cervical region of the spinal cord, wherein the sensitive DR nerve fibers 118 extend straight out from the spinal cord 100, thereby providing more spatial isolation between these nerve fibers and the dorsolateral funiculus 124. As such, the distal tip(s) of the stimulation lead(s) 12 may be more easily located between the DR nerve fiber grouping 116.

Figure 7:
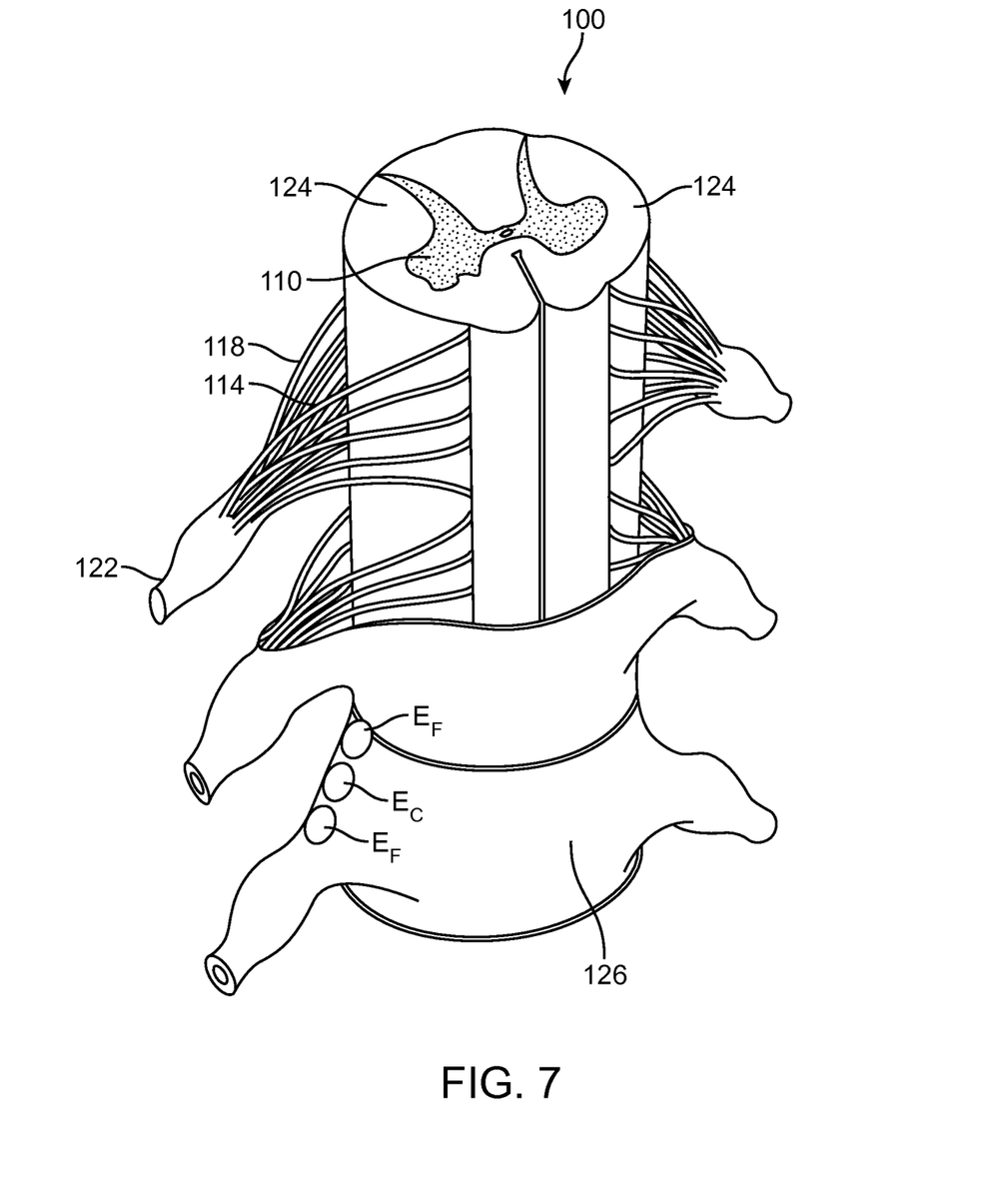
FIG. 7 is a perspective view showing one electrode arrangement relative to the spinal cord and spinal nerves in accordance with the present invention.

Referring to FIG. 7, a configuration of three electrodes (labeled $E_C$ for the center electrode, and $E_F$ for the flanking electrodes) may be arranged relative to a pair of adjacent DR nerve fiber groupings 116, such that it is aligned along the longitudinal axis of the spinal cord 100 (i.e., in the rostro-caudal direction) between the DR nerve groupings 118, such that the flanking electrodes $E_F$ of the tripole configuration are respectively closest to the DR nerve fiber groupings 118. Optionally, e.g., in the case of bilateral pain, another configuration of three electrodes can be aligned along the longitudinal axis of the spinal cord 100 between the DR nerve fiber groupings 118 at the same spinal level on the other lateral side of the spinal cord 100. The electrode configurations can be formed, e.g., using the distal-most electrodes 26 on three side-by-side percutaneous leads 12 (shown in FIG. 3) or the distal-most row of electrodes 26 on the surgical paddle lead 12 (shown in FIG. 4).

As briefly discussed above, the electrodes 26 may be configured in a manner that increases the activation threshold of the DR nerve fiber groupings 118 relative to the activation threshold of the dorsolateral funiculus 124 in order to inhibit the stimulation of DR nerve fiber groupings 118 when the dorsolateral funiculus 124 is stimulated.

The techniques described below apply electrical suppression energy to the DR nerve fiber groupings 118 to decrease their activation threshold. Preferably, the electrodes 26 are placed as closely as possible to the spinal cord 100 in order to maximize the resolution of the energy transmitted by the electrodes 26; that is, to focus the stimulating effect of the stimulation energy on a target site in the dorsolateral funiculus 124, and to focus the activation threshold increasing effect of the suppression energy on the DR nerve fiber groupings 118. Preferably, the proximity of the electrodes 26 to the spinal cord 100 should be less than one-half of the distance between adjacent electrodes 26 to ensure proper resolution. Because the electrodes 26 are typically separated from the spinal cord by the dura 126 and spinal cord fluid, there will typically be some distance between the electrodes 26 and the spinal cord 100, with the distance varying from patient to patient. If implanted within the cervical region of the spine, the proximity of the electrodes 26 to the spinal cord 100 will typically be quite small, and therefore, high resolution can be achieved. If implanted within the thoracic region of the spine, the proximity of the electrodes 26 to the spinal cord 100 will be greater, and therefore, a lower resolution will be achieved.

In one technique for preventing inadvertent stimulation of the DR nerve fiber groupings 118, the electrodes are configured as a tripole, such that the flanking electrodes $E_F$ adjacent the two DR nerve fiber groupings 118 are anodes, and the center electrode $E_C$ is a cathode. In this configuration, electrical stimulation energy conveyed between the cathode(s) and anode(s) creates an electrical field that stimulates the dorsolateral funiculus 124, while preventing stimulation of the DR nerve fiber groupings 118. That is, the electrical current sourced by the outer flanking electrodes $E_F$ hyperpolarizes the DR nerve fiber groupings 118, thereby decreasing their activation threshold, while the electrical current sunk by the center electrode $E_C$ depolarizes the nerve fibers in the dorsolateral funiculus 124, thereby creating a locus of stimulation that is confined to the region of the dorsolateral funiculus 124 adjacent the center electrode $E_C$. In effect, the center electrode $E_C$ generates the electrical stimulation energy at the dorsolateral funiculus 124, while the flanking electrodes $E_F$ "push" the electrical stimulation energy away from the DR nerve fiber groupings 118.

It is desirable that the locus of stimulation be as narrow as possible without increasing its depth, thereby stimulating target nerve fibers within the dorsolateral funiculus, while preventing stimulation of the DR nerve fiber groupings 118. This would require an increase in the electrical current sourced at the flanking electrodes $E_F$. However, this necessarily may result in an increase in the current sunk by the center electrode $E_C$, thereby increasing the depth of the locus of stimulation, which may lead to undesirable outcomes (e.g., discomfort or undesirable reflexive activity). As such, a portion of the electrical current sourced at the flanking electrodes $E_F$ can be additionally sunk at a remote electrode (e.g., the case or even a therapeutic electrode remote from the tripole configuration), thereby creating a local current imbalance at the target site of the dorsolateral funiculus 124.

Further details discussing the use of tripolar electrode arrangements to render tissue less excitable to subsequent stimulation are disclosed in U.S. patent application Ser. No. 11/300,963, entitled "Apparatus and Methods for Stimulating Tissue," which is expressly incorporated herein by reference.

In another technique for preventing inadvertent stimulation of the DR nerve fiber groupings 118, a sub-threshold, hyperpolarizing conditioning pre-pulse can be applied by flanking electrodes $E_F$ to the adjacent DR nerve fiber groupings 118, and a depolarizing stimulation pulse can be subsequently applied by the center electrode $E_C$ to the dorsolateral funiculus 124. The duration between the conditioning pulse and the stimulation pulse is preferably zero, but at the least should be less than 100 μs, and more preferably, less than 30 μs. The conditioning pre-pulse preferably has a relatively short duration, preferably less than 200 μs, more preferably less than 150 μs, and most preferably less than 75 μs, such that m-gates of the sodium ion channels in the neural axons are closed to render the tissue less excitable to subsequent stimulation. The stimulation pulse preferably has a relatively short duration, e.g., less than 200 μs. Optionally, a relatively long depolarizing conditioning pulse preceding the relatively short hyperpolarizing conditioning pulse can be applied by the flanking electrodes $E_F$, such that h-gates of the sodium ion channels in the neural axons are closed to render the tissue even less excitable to subsequent stimulation. To determine the optimum amplitude for the conditioning pre-pulse(s), the amplitude level of the stimulation pulse may be incrementally increased until a side-effect is experienced by the patient, and for each incremental increase in the stimulation pulse, the amplitude of the conditioning pre-pulse(s) may be increased until the side-effect is eliminated or minimized.

Further details discussing the use of conditioning pre-pulses to render tissue less excitable to subsequent stimulation are disclosed in U.S. patent application Ser. No. 11/752, 895, entitled "Short Duration Pre-Pulsing to Reduce Stimulation-Evoked Side-Effects," which is expressly incorporated herein by reference.

In still another technique for preventing inadvertent stimulation of the DR nerve fiber groupings 118, electrical background energy is conveyed from the flanking electrodes $E_F$ in accordance with at least one stochastic parameter. If the electrical background energy is in the form of pulses, the stochastic parameter may comprise at least one of an interpulse interval, pulse amplitude, pulse shape, and pulse duration. If the electrical background energy is white noise, the stochastic parameter may be a frequency.

The three electrodes can be configured as stimulating electrodes in a tripolar arrangement (center electrode $E_C$ as the cathode, and flanking electrodes $E_F$ as the anodes) in a manner described above, while the flanking electrodes $E_F$ can be configured as background electrodes in a monopolar arrangement with the IPG case 40. Thus, electrical stimulation energy is conveyed between the tripolar arrangement of the electrodes, thereby therapeutically stimulating dorsolateral funiculus, and electrical background energy is conveyed between the flanking electrodes $E_F$ and the IPG case 40, thereby decreasing the excitability of the DR nerve fiber groupings 118.

Notably, due to the monopolar arrangement, the field strength of the electrical background energy conveyed from the flanking electrodes $E_F$ decays at a relatively low rate with distance. As such, the flanking electrodes $E_F$ may be relatively far from the DR nerve fiber groupings 118 for them to modulate the excitability of the DR nerve fiber groupings 118. Alternatively, the electrical background energy may be conveyed from flanking electrodes $E_F$ in bipolar arrangement.

However, in this case, due to current shunting, the flanking electrodes $E_F$ must be relatively close to the DR nerve fiber groupings 118. In either case, as a general rule, the excitability of the DR nerve fiber groupings 118 will be decreased if the magnitude of the electrical background energy is relatively high. Alternatively, electrical background energy with a relatively low magnitude may be conveyed from the center electrode $E_C$, thereby increasing the excitability of the dorsolateral funiculus 124. In effect, the activation threshold of the DR nerve fiber groupings 118 will be increased relative to the activation threshold of the dorsolateral funiculus 124 by decreasing the activation threshold of the dorsolateral funiculus 124.

Because the excitability of the DR nerve fiber groupings 118 will be decreased by the electrical background energy, the effect that the inadvertent conveyance of the electrical stimulation energy to the DR nerve fiber groupings 118 will be decreased. In one method, the electrical background energy is set equal to or higher than 10% of the perception threshold of the patient. Preferably, the electrical background energy is sub-threshold (i.e., does not stimulate nerve fibers), but may be supra-threshold if it provides therapy to the patient or can otherwise be tolerated by the patient. Ultimately, the magnitudes of the electrical stimulation energy and electrical background energy can be set relative to each other through trial and error.

Further details discussing the use of electrical background energy to render tissue less excitable to subsequent stimulation are disclosed in U.S. patent application Ser. No. 12/501,127, entitled "System and Method for Reducing Excitability of Dorsal Root Fiber by Introducing Stochastic Background Noise," which is expressly incorporated herein by reference.

In yet another technique for preventing inadvertent stimulation of the DR nerve fiber groupings 118, which works particularly well if the DR nerve fiber groupings 118 extend over the targeted stimulation site of the dorsolateral funiculus 124 (e.g., in the thoracic region), and are therefore closer to the stimulating electrode(s) than the target site of the dorsolateral funiculus 124, the electrical stimulation energy takes the form of high frequency (e.g., in the range of 2-30 KHz) time-varying electrical energy (e.g., a sinuosoidal energy), the frequency and amplitude of which may be selected to increase the activation threshold of the relatively close neural structure (in this case, the DR nerve fiber groupings 118), while stimulating the relatively far neural structure (in this case, the dorsolateral funiculus 124).

This ability is due, in large part, because the blocking threshold of a nerve fiber by high frequency electrical energy is higher than the threshold at which the nerve fiber is activated by the same high frequency electrical energy. Thus, if the high frequency electrical energy has an amplitude that is higher than the blocking threshold of relatively close nerve fibers, the relatively far nerve fibers at a particular depth will still have a blocking threshold above the amplitude of the high frequency electrical energy, but a stimulation threshold below the amplitude of the high frequency electrical energy. This means that relatively close nerve fibers will be blocked at a stimulation current that activates relatively far nerve fibers.

The desired depth range of blocked nerve fibers and the desired depth range of the stimulated nerve fibers may be tuned by selecting the amplitude and frequency of the high frequency electrical energy. In general, as the amplitude of the high frequency electrical energy is increased, the range of distance in which neural structures are blocked increases, and the range of distance in which the neural structures are stimulated decreases.

In one embodiment for determining the optimum amplitude for the high frequency electrical energy, the stimulation amplitude may be increased until the patient reports a segmental effect (e.g., paresthesia) from the stimulation, ostensibly due to activation of the DR nerve fibers 118. Then, the stimulation amplitude may be increased until the patient reports the segmental effect ceases or is negligible. This stimulation amplitude represents the minimum level for therapy. The stimulation amplitude may then be further increased until direct motor activity is segmentally experienced by the patient, ostensibly due to direct activation of the VR nerve fibers 114. This stimulation amplitude represents the maximum level for therapy. The patient may then be free to adjust the stimulation amplitude between these minimum and maximum limits. When stimulation is turned on from an off-state, the stimulation amplitude may be gradually ramped up to minimize the onset of stimulating the sensitive neural structures.

Further details discussing the use of high frequency electrical energy to block action potentials in closer neural tissue while stimulating further neural tissue are disclosed in U.S. patent application Ser. No. 12/819,107, entitled "Spatially Selective Nerve Stimulation in High-Frequency Nerve Conduction Block and Recruitment," which is expressly incorporated herein by reference.

In an optional embodiment, a set of sensors, such as sense amplifiers, accelerometers, chemical sensors, or thermal sensors, may be employed to ensure that the stimulation applied is efficacious, as well as to identify side effects arising from stimulation activity. For example, a sense amplifier coupled to the electrodes 26 may detect ventral or dorsal root activity and subsequently, the stimulation output may be altered to reduce dorsal or ventral root activity.

It should be understood that the SCS system 10 may be utilized alone or in conjunction with other known implantable devices, such as vagal stimulators, pacemakers, defibrillators, sympathetic chain stimulators, brains stimulators, and so on. The SCS system 10 may interact with other stimulator systems, and in one embodiment, all the stimulator systems may be contained within a single system. In such embodiments, the stimulation source and mechanism to control and/or modify stimulation may be applied through a common source. For example, the SCS system 10 may have multiple leads enabling multiple purposes, e.g., an additional stimulation lead or leads positioned over the dorsal column to provide conventional stimulation.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for treating a patient suffering from chronic neuropathic pain, the method comprising:
   implanting at least one stimulation lead in an epidural space of the patient, each stimulation lead comprising a plurality of electrodes disposed along a distal portion of the stimulation lead, wherein the at least one stimulation lead is implanted with at least three of the electrodes disposed lateral of a midline of a spinal cord of the patient in a selected single dorsal-lateral quadrant of the epidural space and adjacent a dorsolateral funiculus of the patient; and applying electrical stimulation energy to the dorsolateral funiculus of the patient, while applying electrical suppression energy to nerve root fibers of the patient, using the at least three electrodes to treat, the chronic neuropathic pain.

2. The method of claim 1, wherein the electrical stimulation energy is applied to a region of the dorsolateral funiculus of the patient rostral to a spinal nerve that innervates a painful region of the patient.

3. The method of claim 1, wherein applying electrical stimulation energy comprises applying the electrical stimulation energy as a time-varying electrical energy having a frequency in a range of 2 to 30 kHz.

4. A method for treating a patient suffering from chronic neuropathic pain, the method comprising:

applying electrical stimulation energy to a dorsolateral funiculus of the patient, thereby treating the chronic neuropathic pain; and increasing the activation threshold of a side-effect exhibiting neural structure relative to the activation threshold of the dorsolateral funiculus of the patient, wherein the electrical stimulation energy is applied to the dorsolateral funiculus of the patient while the activation threshold of the neural structure relative to the dorsolateral funiculus is increased, thereby treating the chronic neuropathic pain without stimulating the neural structure.

5. The method of claim 4, wherein the neural structure is a dorsal root (DR) nerve fiber.

6. The method of claim 4, wherein neural structure is a cervical spinal nerve.

7. The method of claim 4, wherein the activation threshold of the neural structure relative to the activation threshold of the dorsolateral funiculus is increased by applying electrical suppression energy to the neural structure.

8. The method of claim 7, wherein the electrical stimulation energy is applied to dorsolateral funiculus by sinking electrical current at a first electrode adjacent the dorsolateral funiculus, thereby treating the chronic neuropathic pain, and the electrical suppression energy is applied to the neural structure by sourcing at least a portion of the electrical current from a second electrode adjacent the neural structure, thereby increasing the activation threshold of the neural structure.

9. The method of claim 8, wherein electrical suppression energy is applied to a another neural structure adjacent the dorsolateral funiculus to increase the activation threshold of the other neural structure by sourcing at least another portion of the electrical current from a third electrode adjacent the other neural structure, wherein the electrical stimulation energy is applied to the dorsolateral funiculus of the patient while the activation threshold of the other neural structure is increased, thereby treating the chronic neuropathic pain without stimulating the other neural structure.

10. The method of claim 9, wherein neural structure is a first dorsal root (DR) nerve fiber, and the other neural structure is a second dorsal root (DR) nerve fiber.

11. The method of claim 9, wherein the first electrode is a center electrode, and the second and third electrodes are flanking electrodes of a tripole configuration located between the neural structures.

12. The method of claim 9, further comprising sinking at least a portion of the electrical current sourced at the second electrode adjacent the neural structure into a remote electrode.

13. The method of claim 4, wherein the activation threshold of the neural structure is increased by applying a sub-threshold, hyperpolarizing conditioning pre-pulse to the neural structure, and electrical stimulation energy is applied to the dorsolateral funiculus by applying a depolarizing stimulation pulse to the dorsolateral *funiculus*.

14. The method of claim 13, wherein the conditioning pre-pulse has a duration less than 200 µs.

15. The method of claim 4, wherein the activation threshold of the neural structure is increased by applying electrical background energy to the neural structure in accordance with at least one stochastic parameter to the neural structure.

16. The method of claim 15, wherein the electrical background energy comprises pulses, and the at least one stochastic parameter comprises at least one of an interpulse interval, pulse amplitude, pulse shape, and pulse duration.

17. The method of claim 16, wherein the electrical background energy comprises white noise, and the at least one stochastic parameter comprises a frequency.

18. The method of claim 4, wherein the activation threshold of the neural structure is increased by applying time-varying electrical energy having a frequency and amplitude that increases the activation threshold of the neural structure.

19. The method of claim 18, wherein the electrical stimulation energy epidurally applied to the dorsolateral funiculus is the time-varying electrical energy, and the time-varying electrical energy having a frequency and amplitude that increases the activation threshold of the neural structure, while stimulating the relatively dorsolateral *funiculus*.

20. The method of claim 4, wherein applying electrical stimulation energy comprises applying the electrical stimulation energy as a time-varying electrical energy having a frequency in a range of 2 to 30 kHz.

* * * * *